(12) United States Patent
Berger et al.

(10) Patent No.: US 7,670,636 B2
(45) Date of Patent: Mar. 2, 2010

(54) METHOD FOR THE PRODUCTION OF A METALLIC SUBSTRATE HAVING A BIOCOMPATIBLE SURFACE AND SUBSTRATE PRODUCED USING SAME

(75) Inventors: Georg Berger, Panketal (DE); Ute Ploska, Berlin (DE)

(73) Assignee: BAM Bundesanstalt fuer Materialforschung und -pruefung, Berlin (DE)

( * ) Notice: Subject to any disclaimer, the term of this patent is extended or adjusted under 35 U.S.C. 154(b) by 405 days.

(21) Appl. No.: 11/563,884

(22) Filed: Nov. 28, 2006

(65) Prior Publication Data

US 2007/0122638 A1    May 31, 2007

(30) Foreign Application Priority Data

Nov. 29, 2005   (DE)   ................ 10 2005 058 125

(51) Int. Cl.
| | |
|---|---|
| *B05D 7/14* | (2006.01) |
| *B05D 3/02* | (2006.01) |
| *A61L 27/32* | (2006.01) |
| *A61L 27/30* | (2006.01) |
| *A61F 2/28* | (2006.01) |
| *A61F 2/02* | (2006.01) |

(52) U.S. Cl. ................ 427/2.1; 427/2.24; 427/2.26; 427/2.27; 427/2.29; 427/331; 427/372.2; 427/376.1; 623/11.11; 623/16.11; 623/23.57; 623/23.6; 623/23.62

(58) Field of Classification Search .......... 427/2.1–3.1, 427/331, 372.2, 376.1; 623/11.11, 16.11, 623/23.57, 23.6, 23.61, 23.62
See application file for complete search history.

(56) References Cited

U.S. PATENT DOCUMENTS 6,221,111 B1 * 4/2001 Piveteau et al. .......... 623/23.57
6,323,146 B1 * 11/2001 Pugh et al. ..................... 501/1

FOREIGN PATENT DOCUMENTS

| DE | 199 44 970 C1 | 4/2001 |
|---|---|---|
| GB | 1 025 115 | 4/1966 |

OTHER PUBLICATIONS

Guo et al. "Fabrication oand characterization of thin nano-hydroxyapatite coatings on titanium" Surface & Coatings Technology vol. 185 pp. 268-274. May 6, 2004.*

* cited by examiner

*Primary Examiner*—Timothy H Meeks
*Assistant Examiner*—Cachet I Sellman
(74) *Attorney, Agent, or Firm*—Norris McLaughlin & Marcus, PA

(57) ABSTRACT

The invention relates to a method for the production of a metallic substrate having a biocompatible surface and to the substrate that is produced by means of said method. The method comprises treatment of a metal, i.e., Ti, Ti alloys with Al, V, Ta, Nb, Ni, Fe, Mo or mixtures thereof, Ta, Ta alloys with Fe, Al, Cr, stainless steel, with a melt of calcium nitrate and an additional component which is an oxygen salt of Na, K, Li, Mg and mixtures thereof, said treatment being effected at 180-480 ° C. for 0.1 to 12 hours. A substrate is obtained, wherein the overall layer thickness ranges from 10 to below 1600 nm and the fatigue strength of the substrate is in the same fatigue strength range as that of an untreated substrate at equal number of vibrations N.

7 Claims, No Drawings

METHOD FOR THE PRODUCTION OF A METALLIC SUBSTRATE HAVING A BIOCOMPATIBLE SURFACE AND SUBSTRATE PRODUCED USING SAME

BACKGROUND (1) Field of the Invention

The invention relates to a method for the production of a metallic substrate having a biocompatible surface and to the substrate that is produced by means of said method.

(2) Description of Related Art

A method is known from DE 199 44 970 C1, in which method an implant or a substrate made of titanium or Ti alloy is treated with a calcium salt melt to obtain a biocompatible surface. As a result, 1-2 μm layers of $Ca_4Ti_3O_{10}$ are formed.

SUMMARY

The object of the invention is to form thinner layers having high strength and, at the same time, strong adherence and to make this possible with metals other than titanium.

DETAILED DESCRIPTION OF THE INVENTION

According to the invention, the method for the production of a metallic substrate with biocompatible surface comprises treatment of a metal selected from the group consisting of titanium; titanium alloys with aluminum, vanadium, tantalum, niobium, nickel, iron, molybdenum or mixtures thereof; tantalum; tantalum alloys with iron, aluminum, chromium or mixtures thereof; stainless steel;

with a melt consisting of calcium nitrate and an additional component, said additional component being selected from the group consisting of an oxygen salt of sodium, potassium, lithium, magnesium and mixtures thereof;

said treatment being effected at a temperature ranging from 180 to 480° C. for a period of from 0.1 to 12 hours, the calcium content of the melt being at least 20% by weight, relative to the total weight of the melt.

An alloy of titanium with Al and/or V and/or Nb and/or Ni and/or Fe and/or Mo is used as preferred titanium alloy.

An alloy of tantalum with iron and/or aluminum and/or chromium is used as preferred tantalum alloy.

Preferred as additional component is a nitrate or sulfate of Ca, K, Li or Na, with $NaNO_3$ being advantageous. Particularly preferred is a mixture of calcium nitrate and the additional components $NaNO_3$, $KNO_3$, $LiNO_3$ in % by weight: $Ca(NO_3)_2$ 20 to 95; $NaNO_3$ 1 to 50; $KNO_3$ 1 to 50; $LiNO_3$ 0 to 20.

Advantageously, the temperature in this method ranges from 200 to 480° C., preferably from 250 to 460° C. At such low temperatures, there is no enlargement of the layer thickness, but instead, the latter remains approximately constant, altogether resulting in thinner layers than known as yet.

The treatment time advantageously ranges from 0.5 to 8 h, preferably from 0.5 to 4 h, particularly from 0.5 to 2 hours.

When adding one or more oxygen salts of sodium, potassium, lithium or magnesium, it was found that very thin layers of from 5 to 1600 nm, advantageously from 10 to 1000 nm, particularly from 10 to 800 nm, and specifically from 20 to 450 nm can be obtained at temperatures substantially lower than those commonly used so far. The method according to the invention allows coating of such layers not only on titanium or titanium alloys but also on other types of steel suitable for biocompatible application, e.g. on stainless steels or on tantalum steels. With titanium, a layer of $CaTiO_3$ is formed under the conditions specified above.

Tempering as in the well-known process is not required.

The term "oxygen salts" means nitrates, nitrites, sulfates or certain salts of organic acids such as oxalates or hydroxy succinates.

In the method according to the invention, there is no loss in strength as a result of the substantial reduction in temperature and the thinner layers formed thereby. It was found that e.g. the fatigue strength values of 500-600 MPa at a number of vibrations N of $10^7$ to $10^5$ established for untreated titanium alloys are substantially lower for such titanium alloys treated according to DE 19944970, being 400 MPa at $N=10^6$ and 600 MPa at $N=10^5$. In contrast, the materials (titanium, titanium alloys, tantalum, tantalum alloys, stainless steel) treated according to the invention remain in the range of values for the respective untreated materials, thus being clearly superior over the prior art. The fatigue strength was determined using the corresponding test for unnotched round specimen in accordance with DIN 50113-A.

With titanium or titanium alloys, such as Ti—Al—V, Ti—Ta—Nb, Ti—Ni, Ti—Al—Nb, optionally with Mo and/or Fe, the formation of a calcium-containing reaction layer is particularly advantageous because of the accompanying advantageous effects of improving direct bone contact free of connective tissue.

The oxide layer can form chemical compounds with the calcium to produce e.g. calcium titanates. Another advantage is that the method of the invention modifies the absorptive behavior of proteins on the reaction layers, allowing more rapid, biologically adapted ingrowth of a substrate.

By virtue of the method according to the invention, there is less rapid or barely any decomposition of the melt, i.e. the formation of nitrous gases is significantly slowed down. Furthermore, considering the treatment times involved, a wider temperature interval is available for the production of the reaction layer on the metal substrate.

The invention is also directed to a metallic substrate having a biocompatible surface, on which substrate, being selected from the group consisting of titanium; titanium alloys with aluminum, vanadium, tantalum, niobium, nickel, iron, molybdenum or mixtures thereof; tantalum; tantalum alloys with iron, aluminum, chromium or mixtures thereof; stainless steel;

a reaction layer is formed, consisting of an inner oxide layer facing the substrate and an outer Ca-containing layer, the overall layer thickness ranging from 10 to below 1600 nm. On its outwardly facing surface, the outer Ca-containing layer may have Na, K, Li, Mg atoms or mixtures thereof incorporated therein, thereby influencing the solubility/stability of the implant/bone interface in a lasting fashion and modifying the flux of ions transferred into the body fluid in terms of quality and quantity.

The Ca-containing layer is a reaction layer integrated in the oxide layer and produced from the reaction of a fused Ca salt with the oxide surface layer. As a rule, the oxide surface layer on the metal basic body is increased by the elevated temperature during the process and under the influence of the salt melt, i.e., the measurable thickness of this layer increases. Consequently, this layer is not a coated layer situated on top of the surface, but rather is integrated into the metal surface (reaction layer). Other elements can be integrated in this layer down to a specific depth of the layer. Advantageously, the layer is made significantly thinner in the substrate according to the invention, ranging from 10 to 1500 nm, particularly from 10 to 800 nm, and specifically from 20 to 450 nm.

Another feature of the substrate is that the fatigue strength thereof is in the range of the fatigue strength of the untreated substrate.

Preferred is a metallic substrate consisting of titanium or a titanium-containing alloy, wherein the Ca-containing layer consists of calcium titanate as major component and the outwardly facing surface thereof may have Na, K, Li, Mg atoms or mixtures thereof incorporated therein. The other metals or metal alloys may contain similar inclusions.

With reference to the examples, the invention will be illustrated in more detail below. The percentages specified therein are percents by weight (wt.-%).

EXAMPLE 1

A degreased, washed and dried sample of $TiAl_6V_4$ is kept in a salt melt of calcium nitrate tetrahydrate (74 wt.-%) and sodium nitrate (26 wt.-%) for 4 h at 450° C. Subsequently, it is purified with hot water in an ultrasonic bath (10 min) and with dilute hydrochloric acid (1 part of conc. HCl and 9 parts of water; conc.=concentrated hydrochloric acid, a 37% hydrochloric acid being referred to as conc. hydrochloric acid), likewise in an ultrasonic bath (5 min), washed with completely desalted water and subsequently with absolute alcohol and dried. Using X-ray diffractometry on thin layers (TF-XRD), formation of calcium titanate was detected on the surface. The layer thickness of the oxide Ca-containing layer was 190 nm, measured using AUGER electron spectroscopy.

EXAMPLE 2

A degreased, washed and dried sample of NiTi is kept in a salt melt of calcium nitrate tetrahydrate (74 wt.-%) and sodium nitrate (26 wt.-%) for 4 h at 480° C. Subsequently, it is purified with hot water in an ultrasonic bath (10 min) and with dilute hydrochloric acid (1 part of (conc.) HCl and 9 parts of water; also in the following examples), likewise in an ultrasonic bath (5 min), washed with completely desalted water and subsequently with absolute alcohol and dried. Using TF-XRD, formation of calcium titanate was detected on the surface.

EXAMPLE 3

A degreased, washed and dried sample of $TiAl_6V_4$ is kept in a salt melt of calcium nitrate (63 wt.-%), sodium nitrate (17 wt.-%) and potassium nitrate (23 wt.-%) for 2 h at 400° C. Subsequently, it is purified with hot water in an ultrasonic bath (10 min) and with dilute hydrochloric acid (1 part of HCl+9 parts of water), likewise in an ultrasonic bath (5 min), washed with completely desalted water and subsequently with absolute alcohol and dried. Layer thickness (as in Example 1) 150 nm, measured using AUGER electron spectroscopy. Furthermore, Ca was detected by means of AUGER electron spectroscopy in the substrate surface down to a depth of 15 nm.

EXAMPLE 4

A degreased, washed and dried sample of high-purity (cp) titanium is kept in a salt melt of calcium nitrate (70 wt.-%), sodium nitrate (12 wt.-%), potassium nitrate (12 wt.-%) and lithium nitrate (6 wt.-%) for 2 h at 250° C. Subsequently, it is purified with hot water in an ultrasonic bath (10 min) and with dilute hydrochloric acid (1 part of HCl+9 parts of water), likewise in an ultrasonic bath (5 min), washed with completely desalted water and subsequently with absolute alcohol and dried. The layer thickness (as in Example 1) was 20 nm, measured using AUGER electron spectroscopy.

EXAMPLE 5

A degreased, washed and dried sample of implant steel is kept in a salt melt of calcium nitrate tetrahydrate (74 wt.-%) and sodium nitrate (26 wt.-%) for 2 h at 450° C. Subsequently, it is purified with hot water in an ultrasonic bath (10 min) and with dilute hydrochloric acid (1 part of HCl and 9 parts of water), likewise in an ultrasonic bath (5 min), washed with completely desalted water and subsequently with absolute alcohol and dried.

Using electron spectrometry (ESCA), calcium and sodium were detected in the layer close to the surface. The layer thickness of the oxide Ca-containing layer was 290 nm, measured using AUGER electron spectroscopy.

EXAMPLE 6

A degreased, washed and dried sample of tantalum sheet is kept in a salt melt of calcium nitrate (70 wt.-%) and sodium nitrate (12 wt.-%) for 4 h at 480° C. Subsequently, it is purified with hot water in an ultrasonic bath (10 min) and with dilute hydrochloric acid (1 part of HCl+9 parts of water), likewise in an ultrasonic bath (5 min), washed with completely desalted water and subsequently with absolute alcohol and dried.

Using TF-XRD, formation of calcium tantalate was detected on the surface. The layer thickness of the oxide Ca-containing layer was 220 nm, measured using AUGER electron spectroscopy.

EXAMPLE 7

A degreased, washed and dried sample of $TiAl_6V_4$ is kept in a salt melt of calcium nitrate (63 wt.-%), sodium nitrate (17 wt.-%) and potassium nitrate (23 wt.-%) for 25 min at 250° C. subbsequently, it is purified with hot water in an ultrasonic bath (10 min) and with dilute hydrochloric acid (1 part of HCl+9 parts of water), likewise in an ultrasonic bath (5 min), washed with completely desalted water and subsequently with absolute alcohol and dried.

Using AUGER electron spectrometry, Ca was detected in the substrate surface down to a depth of 8 nm.

The invention claimed is:

1. A method for the production of a metallic substrate with biocompatible surface, the method comprising
    providing a metal selected from the group consisting of:
        titanium;
        titanium alloys with aluminum, vanadium, tantalum, niobium, nickel, iron, molybdenum or mixtures thereof;
        tantalum;
        tantalum alloys with iron, aluminum, chromium or mixtures thereof; and
        stainless steel, and
    treating the metal with a melt at a temperature ranging from 180 to 480° C. for a period of from 0.1 to 12 hours, wherein the melt consists of calcium nitrate and an additional component, wherein the additional component is selected from the group consisting of an oxygen salt of sodium, potassium, lithium, magnesium and mixtures thereof, wherein a calcium content of the melt is at least 20% by weight, relative to a total weight of the melt.

2. The method according to claim 1, wherein the titanium alloy is selected from the group consisting of an alloy of titanium with aluminum and vanadium, an alloy of titanium with niobium, an alloy of titanium with nickel, and an alloy of titanium with niobium, tantalum and zirconium.

3. The method according to claim 1, wherein the tantalum alloy is an alloy of tantalum with one or more of the elements, iron, aluminum and chromium.

4. The method according to claim 1, wherein the additional component is $NaNO_3$.

5. The method according to claim 4, wherein the calcium nitrate is present at an amount of 20 to 95 wt.-% and sodium nitrate is present at an amount of 1 to 50 wt.-%.

6. The method according to claim 1, wherein the additional component is $NaNO_3$, $KNO_3$ and $LiNO_3$.

7. The method according to claim 6, wherein $Ca(NO_3)_2$ is present in an amount of 20 to 95 wt.-%, $NaNO_3$ is present in an amount of 1 to 50 wt.-%, $KNO_3$ is present in an amount of 1 to 50 wt.-%, and $LiNO_3$ is present in an amount of 0 to 20 wt.-%.

* * * * *